(12) United States Patent
Ishiwata

(10) Patent No.: US 10,064,803 B2
(45) Date of Patent: Sep. 4, 2018

(54) COPOLYMER FOR COSMETICS, SURFACE TREATMENT AGENT FOR COSMETIC POWDER, POWDER FOR COSMETICS, AND COSMETIC PREPARATION

(75) Inventor: Fusae Ishiwata, Kanagawa (JP)

(73) Assignee: AGC SEIMI CHEMICAL CO., LTD., Kanagawa (JP)

( * ) Notice: Subject to any disclaimer, the term of this patent is extended or adjusted under 35 U.S.C. 154(b) by 640 days.

(21) Appl. No.: 14/241,738

(22) PCT Filed: Aug. 22, 2012

(86) PCT No.: PCT/JP2012/071158
§ 371 (c)(1),
(2), (4) Date: Feb. 27, 2014

(87) PCT Pub. No.: WO2013/031594
PCT Pub. Date: Mar. 7, 2013

(65) Prior Publication Data
US 2014/0228450 A1   Aug. 14, 2014

(30) Foreign Application Priority Data
Aug. 29, 2011   (JP) .................................. 2011-186509

(51) Int. Cl.
| | |
|---|---|
| *A61K 8/81* | (2006.01) |
| *A61K 8/02* | (2006.01) |
| *A61Q 1/12* | (2006.01) |
| *A61Q 1/00* | (2006.01) |
| *C08F 220/22* | (2006.01) |

(52) U.S. Cl.
CPC .......... *A61K 8/8152* (2013.01); *A61K 8/0241* (2013.01); *A61Q 1/00* (2013.01); *A61Q 1/12* (2013.01); *C08F 220/22* (2013.01); *A61K 2800/624* (2013.01)

(58) Field of Classification Search
CPC ...... A61K 8/8152; A61K 8/0241; A61Q 1/00; A61Q 1/12; C08F 220/22
See application file for complete search history.

(56) References Cited

U.S. PATENT DOCUMENTS

| 2011/0110995 A1 | 5/2011 | Hasegawa et al. |
|---|---|---|
| 2012/0149860 A1 | 6/2012 | Ishiwata et al. |

FOREIGN PATENT DOCUMENTS

| JP | 62 250074 | 10/1987 |
|---|---|---|
| JP | 2 218603 | 8/1990 |
| JP | 7 134209 | 5/1995 |
| JP | 2000 290137 | 10/2000 |
| JP | 2004 323646 | 11/2004 |
| JP | 2007 210939 | 8/2007 |
| JP | 2010 222382 | 10/2010 |
| WO | 2009 142047 | 11/2009 |

OTHER PUBLICATIONS

International Search Report dated Oct. 30, 2012 in PCT/JP12/071158 Filed Aug. 22, 2012.

*Primary Examiner* — Rachael Eva Bredefeld
(74) *Attorney, Agent, or Firm* — Oblon, McClelland, Maier & Neustadt, L.L.P.

(57) ABSTRACT

The purpose of the present invention is to provide: a copolymer for cosmetics, which has excellent water repellency and oil repellency even though a polyfluoroalkyl group therein has 6 or less carbon atoms; a surface treatment agent which contains the copolymer for cosmetics; a powder for cosmetics, which is treated with the surface treatment agent and has excellent water repellency and oil repellency; and a cosmetic preparation which contains the powder for cosmetics. A copolymer for cosmetics of the present invention contains: 70-90% by mass of a constituent unit (A) that is derived from a compound represented by formula (a); 2-25% by mass of a constituent unit (B) that is derived from a compound represented by formula (b); 2-25% by mass of a constituent unit (C) that is derived from a compound represented by formula (c); 0.1-10% by mass of a constituent unit (D) that is derived from a compound represented by formula (d); and a residue (E) of a chain-transfer agent (e) that contains an OH group or a COOH group.

$CH_2=CR^1-COO-Q^1-Rf$ (a)

$CH_2=CR^2-Q^2-COOH$ (b)

$CH_2=CR^3-COO-(R^4O)n-R^5$ (c)

$CH_2=CR^7-COO-Q^3-P(O)(OH)-R^8$ (d)

11 Claims, No Drawings

COPOLYMER FOR COSMETICS, SURFACE TREATMENT AGENT FOR COSMETIC POWDER, POWDER FOR COSMETICS, AND COSMETIC PREPARATION

TECHNICAL FIELD

The present invention relates to a copolymer for cosmetics, a surface treatment agent containing the same, a cosmetic powder treated with the surface treatment agent, and a cosmetic preparation containing the cosmetic powder.

BACKGROUND ART

It has been conventionally known that a cosmetic powder for use in a cosmetic preparation is surface-treated with a fluorine-containing compound or the like to impart the water resistance, sebum resistance and oil resistance to the cosmetic preparation, thereby preventing makeup from coming off. For example, a perfluoroalkyl phosphate and a perfluoroalkyl silane are disclosed as the fluorine-containing compounds (see Patent Literatures 1 and 2).

The perfluoroalkyl group-containing compounds generally exhibit higher hydrophobicity and oleophobicity with increasing the chain length of the group but biological and environmental accumulativity of perfluorooctanoic acid (PFOA) has recently attracted attention, and in March 2003, United States Environmental Protection Agency (USEPA) published a preliminary risk assessment on the safety of PFOA, and in January 2006, USEPA advocated participation in the program for reducing environmental emission of PFOA and related chemicals as well as their precursors, and reducing their contents in the products to fluororesin manufactures and the like. Therefore, it is becoming more and more difficult to obtain and use a compound having a perfluoroalkyl group with a chain length of 8 or more carbon atoms.

A powder using a polymer having a perfluoroalkyl group with a chain length of 6 carbon atoms is also proposed (see Patent Literature 3). However, these literatures do not achieve sufficient water and oil repellency.

CITATION LIST

Patent Literature

Patent Literature 1: JP 62-250074 A
Patent Literature 2: JP 2-218603 A
Patent Literature 3: JP 2007-210939 A

SUMMARY OF INVENTION

Technical Problems

An object of the present invention is to provide a copolymer for cosmetics having excellent water and oil repellency although the number of carbon atoms in a polyfluoroalkyl group is 6 or less, and a surface treatment agent containing the copolymer. Another object of the present invention is to provide a cosmetic powder treated with the foregoing surface treatment agent and having excellent water and oil repellency and a cosmetic preparation containing the cosmetic powder.

Solution to Problems

The present invention provides a copolymer for cosmetics comprising: 70 to 90 wt % of a constituent unit (A) derived from a compound represented by formula (a) shown below; 2 to 25 wt % of a constituent unit (B) derived from a compound represented by formula (b) shown below; 2 to 25 wt % of a constituent unit (C) derived from a compound represented by formula (c) shown below; 0.1 to 10 wt % of a constituent unit (D) derived from a compound represented by formula (d) shown below; and a residue (E) of an OH group- or COOH group-containing chain transfer agent (e), $$CH_2=CR^1-COO-Q^1-Rf \quad (a)$$

in formula (a),
$Q^1$ is a single bond or a divalent linking group;
$R^1$ is a hydrogen atom or a methyl group; and
Rf is a polyfluoroalkyl group having 1 to 6 carbon atoms or a polyfluoroether group, $$CH_2=CR^2-Q^2-COOH \quad (b)$$

$Q^2$ is a single bond or a divalent linking group; and
$R^2$ is a hydrogen atom, a methyl group or a COOH group, $$CH_2=CR^3-COO-(R^{40})n-R^5 \quad (c)$$

$R^3$ is a hydrogen atom or a methyl group;
$R^4$ is an alkylene group having 2 to 4 carbon atoms in which a part or all of hydrogen atoms is optionally substituted with OH groups;
n is from 1 to 300;
$R^5$ is a hydrogen atom, an alkyl group having 1 to 4 carbon atoms or a group represented by formula (s) shown below:

$$-CO-CR^6=CH_2 \quad (s); \text{ and}$$

$R^6$ is a hydrogen atom or a methyl group,
provided that $R^4$ groups in a number of n in one molecule of the compound represented by formula (c) are identical or different, $$CH_2=CR^7-COO-Q^3-P(O)(OH)-R^8 \quad (d)$$

$Q^3$ is a single bond or a divalent linking group;
$R^7$ is a hydrogen atom or a methyl group;
$R^8$ is an OH group or a group represented by formula (t) shown below:

$$-Q^4-OCO-CR9=CH2 \quad (t)$$

$Q^4$ is a single bond or a divalent linking group; and
$R^9$ is a hydrogen atom or a methyl group.

The copolymer for cosmetics according to (1), wherein
$Q^1$ in formula (a) is a single bond or a linear or branched alkylene group having 1 to 10 carbon atoms;
$Q^2$ in formula (b) is a single bond, an alkylene group having 1 to 10 carbon atoms, or a group represented by $-(C_2H_4O)_p-$ or $-COO-Q^6-$;
$R^4$ in formula (c) is an alkylene group having 2 or 3 carbon atoms; and
$Q^3$ in formula (d) is a single bond, an alkylene group having 1 to 10 carbon atoms or $-(C_2H_4O)_p-$ (where p is from 1 to 10 (on average)),
provided that $Q^6$ is defined as follows:
$Q^6$ is a linear or branched alkylene group having 1 to 10 carbon atoms, $-(C_2H_4O)_p-$, $-(C_3H_6O)_q-$ (where p and q are each independently from 1 to 10 (on average)), a 6-membered aromatic cyclic group, a 4- to 6-membered saturated or unsaturated aliphatic cyclic group, a 5- to 6-membered heterocyclic group, a cyclic group formed by condensation thereof, a divalent linking group represented by formula (u2) or (u3) shown below, or a combination thereof, and $Q^6$ optionally has a substituent, $$-Y^1-Z^1- \quad (u2)$$

$$-Y^1-Z^1-Y^2- \quad (u3)$$

$Y^1$, $Y^2$ and $Z^1$ in the formulae are defined as follows:

$Y^1$ is a linear or branched alkylene group having 1 to 10 carbon atoms, —$(C_2H_4O)_p$—, —$(C_3H_6O)_q$— (where p and q are each independently from 1 to 10 (on average)), a 6-membered aromatic cyclic group, a 4- to 6-membered saturated or unsaturated aliphatic cyclic group, a 5- to 6-membered heterocyclic group, or a cyclic group formed by condensation thereof;

$Y^2$ is a linear or branched alkylene group having 1 to 10 carbon atoms, a 6-membered aromatic cyclic group, a 4- to 6-membered saturated or unsaturated aliphatic cyclic group, a 5- to 6-membered heterocyclic group, or a cyclic group formed by condensation thereof; and $Z^1$ is —O—, —S—, —CO—, —COO—, —COS—, —N(R)—, —SO$_2$—, —PO$_2$—, —N(R)—COO—, —N(R)—CO—, —N(R)—SO$_2$—, —N(R)—PO$_2$—, where R is a hydrogen atom or an alkyl group having 1 to 3 carbon atoms, provided that $Z^1$ is optionally oriented in an opposite direction, and these groups ($Y^1$, $Y^2$ and $Z^1$) optionally have a substituent.

The polyfluoroalkyl group in formula (a) is preferably a perfluoroalkyl group.

$Q^1$ in formula (a) is preferably a linear alkylene group having 1 to 10 carbon atoms.

The chain transfer agent (e) is preferably isopropanol.

The present invention also provides a surface treatment agent for cosmetic powder comprising: the above-described copolymer for cosmetics and a solvent.

The present invention also provides a cosmetic powder comprising attached thereto the above-described copolymer for cosmetics.

The present invention also provides a cosmetic preparation comprising the above-described cosmetic powder.

Advantageous Effects of Invention

The copolymer for cosmetics according to the present invention contains a polyfluoroalkyl group having a chain length of up to 6 carbon atoms and can ensure ecological and environmental safety. The surface treatment agent containing the copolymer for cosmetics made it possible to impart sufficient water and oil repellency to cosmetic powder.

DESCRIPTION OF EMBODIMENTS

A copolymer for cosmetics according to the invention includes 70 to 90 wt % of a constituent unit (A) derived from a compound represented by formula (a) shown above; 2 to 25 wt % of a constituent unit (B) derived from a compound represented by formula (b) shown above; 2 to 25 wt % of a constituent unit (C) derived from a compound represented by formula (c) shown above; 0.1 to 10 wt % of a constituent unit (D) derived from a compound represented by formula (d) shown above; and a residue (E) of an OH group- or COOH group-containing chain transfer agent (e).

In the present specification, the compound represented by formula (a) is also written as "compound (a)" and the compounds represented by the other formulae may also be written in the same manner as above. Moreover, acryl and methacryl may be collectively referred to as "(meth)acryl." The copolymer for cosmetics according to the invention may also be referred to as "copolymer of the invention."

In formula (a), $Q^1$ is a single bond or a divalent linking group. $Q^1$ can be appropriately selected if it is a single bond or a divalent linking group, and $Q^1$ is not limited thereto.

Examples of the divalent linking group include a linear or branched alkylene group having 1 to 10 carbon atoms, an alkenylene group having 2 to 10 carbon atoms, —$(C_2H_4O)_p$—, —$(C_3H_6O)_q$— (where p and q are each independently from 1 to 10 (on average)), a 6-membered aromatic cyclic group, a 4- to 6-membered saturated or unsaturated aliphatic cyclic group, a 5- to 6-membered heterocyclic group, and a divalent linking group represented by formula (u1) shown below. These divalent linking groups may be combined, and the cyclic groups may be condensed.

$$—Y—Z—  \quad (u1)$$

The symbols in the formula have the following meanings:

Y: A linear or branched alkylene group having 1 to 10 carbon atoms, a 6-membered aromatic cyclic group, a 4- to 6-membered saturated or unsaturated aliphatic cyclic group, a 5- to 6-membered heterocyclic group, or a cyclic group formed by condensation thereof.

Z: —O—, —S—, —CO—, —COO—, —COS—, —N(R)—, —SO$_2$—, —PO$_2$—, —N(R)—COO—, —N(R)—CO—, —N(R)—SO$_2$—, —N(R)—PO$_2$—.

R: A hydrogen atom or an alkyl group having 1 to 3 carbon atoms.

However, Z may be oriented in an opposite direction.

The divalent linking group may have a substituent, examples thereof including halogen atoms (F, Cl, Br, I), cyano group, alkoxy groups (e.g., methoxy, ethoxy, butoxy, octyloxy, methoxyethoxy), aryloxy groups (e.g., phenoxy), alkylthio groups (e.g., methylthio, ethylthio), acyl groups (e.g., acetyl, propionyl, benzoyl), sulfonyl groups (e.g., methanesulfonyl, benzenesulfonyl), acyloxy groups (e.g., acetoxy, benzoyloxy), sulfonyloxy groups (e.g., methanesulfonyloxy, toluenesulfonyloxy), phosphonyl groups (e.g., diethylphosphonyl), amido groups (acetylamino, benzoylamino), carbamoyl groups (e.g., N,N-dimethylcarbamoyl, N-phenylcarbamoyl), alkyl groups (e.g., methyl, ethyl, propyl, isopropyl, cyclopropyl, butyl), aryl groups (e.g., phenyl, toluoyl), heterocyclic groups (e.g., pyridyl, imidazolyl, furanyl), alkenyl groups (e.g., vinyl, 1-propenyl), alkoxyacyloxy groups (e.g., acetyloxy), alkoxycarbonyl groups (e.g., methoxycarbonyl, ethoxycarbonyl), and polymerizable groups (e.g., vinyl group, acryloyl group, methacryloyl group, silyl group, cinnamic acid residue).

$Q^1$ can be appropriately selected if it is a single bond or a divalent linking group. In particular, $Q^1$ is preferably a single bond or a linear or branched alkylene group having 1 to 10 carbon atoms, and most preferably a linear alkylene group having 1 to 10 carbon atoms.

In formula (a), $R^1$ is a hydrogen atom or a methyl group. $R^1$ may be a hydrogen atom or a methyl group.

In formula (a), Rf is a polyfluoroalkyl group having 1 to 6 carbon atoms or a polyfluoroether group. The polyfluoroalkyl group as used herein refers to a partially fluoro-substituted or perfluoro-substituted alkyl group in which two to all of hydrogen atoms in the alkyl group are substituted with fluorine atoms. The polyfluoroalkyl group may be of a linear structure or a branched structure. It should be noted that, in the case of the branched structure, the number of carbon atoms in the polyfluoroalkyl group includes the number of carbon atoms in the branched structure.

Examples of the linear structure include methyl group, ethyl group, n-propyl group, n-butyl group, n-pentyl group and n-hexyl group. Examples of the branched structure include isopropyl group, s-butyl group, t-butyl group, 3-methylbutyl group, isopentyl group, neopentyl group and isohexyl group.

The polyfluoroether group refers to a group in which an ethereal oxygen atom is inserted between carbon atoms in one or more moieties of the polyfluoroalkyl group.

The number of carbon atoms in the polyfluoroalkyl group includes all of carbon atoms to which fluorine atoms are bonded and is determined so that the number of carbon atoms included in this group may be the minimum.

For instance, in a case where "-$Q^1$-Rf" in formula (a) is a group represented by "—$C_2H_4$—$C_6F_{13}$," $Q^1$ is "$C_2H_4$" and Rf is "$C_6F_{13}$." Likewise, in a case where "-$Q^1$-Rf" is a group represented by "—$CH_2$—CHF—$CH_2$—$CF_2H$", $Q^1$ is "$CH_2$" and Rf is "CHF—$CH_2$—$CF_2H$."

Rf may be of a linear structure or a branched structure but is preferably of a linear structure in order to increase the packing of the Rf group. For the same reason as above, in the case of a branched structure, a case in which a branched moiety is present at an end portion of the Rf group is preferable.

The Rf group is preferably a polyfluoroalkyl group in terms of excellent oil repellency. In addition, the Rf group is preferably a perfluoroalkyl group ($R^F$ group) in which all hydrogen atoms are substantially substituted with fluorine atoms, and more preferably a linear Rf group.

Rf is preferably —$C_6F_{13}$ or —$C_4F_9$ in terms of more excellent water and oil repellency.

A suitable example of the compound (a) includes a compound represented by formula (a1) shown below:

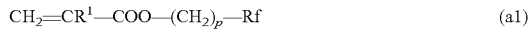
(a1)

In formula (a1), p is an integer of 0 to 6, and $R^1$ and Rf are as defined in formula (a).

Of the above-defined compounds, a compound of a structure in which Rf is a linear perfluoroalkyl group ($R^F$) having 1 to 6 carbon atoms is appropriate. To be more specific, the following compounds are illustrated in terms of excellent water and oil repellency.

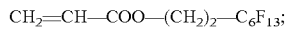

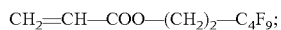

and the like.

The compounds (a) may be used alone or in combination of two or more thereof.

The content of the constituent unit (A) in the copolymer of the invention is preferably from 75 to 85 wt % because when the content of the constituent unit (A) in the polymer of the invention is within the foregoing range, a surface treatment agent containing the polymer of the invention has good water and oil repellency.

In cases where two or more types of constituent units (A) are present by the use of two or more types of compounds (a), the total content is preferably within the foregoing range.

In the present invention, the content of each of the constituent units in the polymer is determined assuming that all the materials used in the polymerization make up the constituent units. Therefore, in a case where the content of the constituent unit (A) is expressed, for example, by the weight ratio (percentage of the weight of the constituent unit (A) contained therein with respect to the total weight of the constituent units), the content is determined as the ratio of the weight of the compound (a) used in the polymerization to the total weight of the compounds used as the polymerization materials. The weight ratios of the other constituent units in the polymer are also determined in the same manner. When a plurality of types of constituent units (A) are present, the content of the constituent units (A) refers to a total amount of the constituent units (A).

In formula (b), $Q^2$ is a single bond or a divalent linking group and examples of the divalent linking group include those defined for $Q^1$ in formula (a). Other examples include a divalent linking group represented by formula (u2) or (u3) shown below, or a combination thereof. In a case where the compound represented by formula (b) has an ester bond in $Q^2$, according to a preferred embodiment, a divalent linking group represented by formula (u2) or (u3) or a combination thereof is bonded to the ester bond and —COOH therebetween.

$R^2$ is a hydrogen atom, a methyl group or a COOH group.

$Q^2$ is preferably a single bond, an alkylene group having 1 to 10 carbon atoms, —$(C_2H_4O)_p$—, or —COO-$Q^6$- to be described later.

The compound (b) is preferably a compound represented by formula (b1) or (b2) shown below.

(b1)

In this formula, $R^2$ is as defined above, $Q^5$ is a single bond when $R^2$ is a hydrogen atom or a methyl group, and is an alkylene group having 1 to 10 carbon atoms when $R^2$ is a COOH group.

(b2)

In this formula, $R^2$ is as defined above, $Q^6$ is a linear or branched alkylene group having 1 to 10 carbon atoms, —$(C_2H_4O)_p$—, —$(C_3H_6O)_q$— (where p and q are each independently from 1 to 10 (on average)), a 6-membered aromatic cyclic group, a 4- to 6-membered saturated or unsaturated aliphatic cyclic group, a 5- to 6-membered heterocyclic group, a cyclic group formed by condensation thereof, a divalent linking group represented by formula (u2) or (u3) shown below, or a combination thereof. $Q^6$ may have a substituent such as a hydroxyl group or an aryl group. Specific examples thereof include an alkylene group, —$(C_2H_4O)_p$—, —$(C_3H_6O)_q$—, a 6-membered aromatic cyclic group, a 4- to 6-membered saturated or unsaturated aliphatic cyclic group, a 5- to 6-membered heterocyclic group, a cyclic group formed by condensation thereof, a divalent linking group represented by formula (u2) or (u3) shown below, or a combination thereof, which have a substituent such as a hydroxyl group or an aryl group.

(u2)

(u3)

$Y^1$, $Y^2$ and $Z^1$ in the formulae have the following meanings:
$Y^1$: A linear or branched alkylene group having 1 to 10 carbon atoms, —$(C_2H_4O)_p$—, —$(C_3H_6O)_q$— (where p and q are each independently from 1 to 10 (on average)), a 6-membered aromatic cyclic group, a 4- to 6-membered saturated or unsaturated aliphatic cyclic group, a 5- to 6-membered heterocyclic group, or a cyclic group formed by condensation thereof.
$Y^2$: A linear or branched alkylene group having 1 to 10 carbon atoms, a 6-membered aromatic cyclic group, a 4- to 6-membered saturated or unsaturated aliphatic cyclic group, a 5- to 6-membered heterocyclic group, or a cyclic group formed by condensation thereof.
$Z^1$: —O—, —S—, —CO—, —COO—, —COS—, —N(R)—, —$SO_2$—, —$PO_2$—, —N(R)—COO—, —N(R)—CO—, —N(R)—$SO_2$—, —N(R)—$PO_2$—.

R: A hydrogen atom or an alkyl group having 1 to 3 carbon atoms.

However, $Z^1$ may be oriented in an opposite direction. These groups ($Y^1$, $Y^2$ and $Z^1$) may have a substituent such as a hydroxyl group or an aryl group.

In formula (b2), a case in which $Y^1$ in formula (u3) is an alkylene group having 1 to 10 carbon atoms or —$(C_2H_4O)_p$— (where p is from 1 to 10 (on average)); $Y^2$ in formula (u3) is an alkylene group having 1 to 10 carbon atoms, a phenylene group or a cyclohexylene group; and $Z^1$ in formula (u3) is —CO—, —COO— or —OCO—, respectively, is preferable.

Specific examples of the compound (b1) include the following:

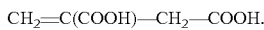

Specific examples of the compound (b2) include the following:

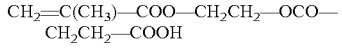

[Chemical Formula 1]

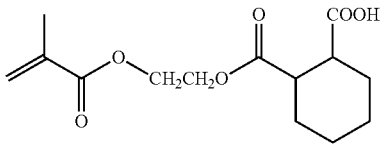

[Chemical Formula 2]

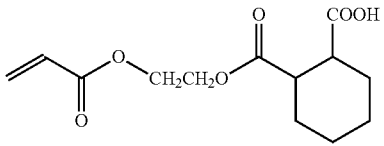

[Chemical Formula 3]

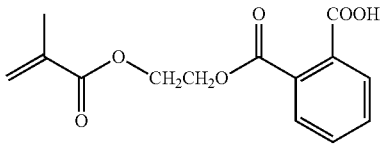

[Chemical Formula 4]

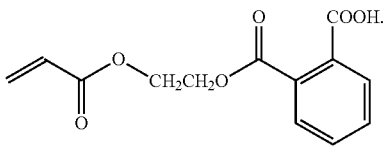

The compound (b) is preferably a compound illustrated as the compound (b1) and most preferably acrylic acid because the water and oil repellency is further improved.

The compounds (b) may be used alone or in combination of two or more thereof.

The content of the constituent unit (B) in the copolymer of the invention is preferably from 5 to 15 wt % because when the content of the constituent unit (B) in the polymer of the invention is within the foregoing range, the water and oil repellency of the surface treatment agent containing the polymer of the invention is improved.

In cases where two or more types of constituent units (B) are present by the use of two or more types of compounds (b), the total content is preferably within the foregoing range.

In formula (c), $R^3$ is a hydrogen atom or a methyl group. $R^4$ is an alkylene group having 2 to 4 carbon atoms in which a part or all of hydrogen atoms may be substituted with OH groups. n is from 1 to 300, and —$(R^4O)_n$— may be made up of one type of alkylene group or a plurality of types of alkylene groups which are different in the number of carbon atoms. $R^5$ is a hydrogen atom, an alkyl group having 1 to 4 carbon atoms or a group represented by formula (s) shown below:

where $R^6$ is a hydrogen atom or a methyl group.

$R^4$ is preferably an alkylene group having 2 or 3 carbon atoms and most preferably an alkylene group having 2 carbon atoms. n is preferably from 1 to 100, more preferably from 1 to 25 and most preferably from 2 to 10. In a case where —$(R^4O)_n$— is made up of a plurality of types of alkylene groups which are different in the number of carbon atoms, the number of times each of the alkyleneoxy groups different in the number of carbon atoms is repeated as the recurring unit (for instance, m, l, o, p and q in specific examples shown below) can be set to 1 to 100. n shows an average value. $R^5$ is preferably a hydrogen atom, a methyl group or a group represented by formula (s) and most preferably a hydrogen atom.

Specific examples of the compound (c) include the following compounds:

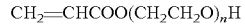

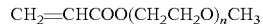

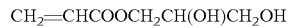

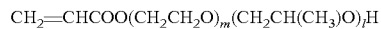

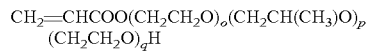

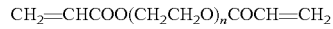

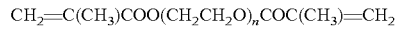

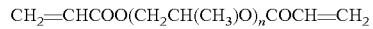

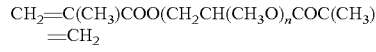

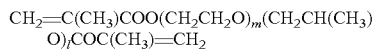

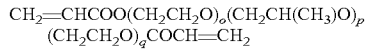

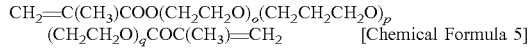 [Chemical Formula 5]

(where n, m, l, o, p and q are each independently from 1 to 100 (on average).)

The compound (c) in which $R^4$ is an alkylene group having 2 carbon atoms, n is from 2 to 10 (on average) and $R^5$ is a hydrogen atom is preferable because the water and oil repellency is improved.

The compounds (c) may be used alone or in combination of two or more thereof.

The content of the constituent unit (C) in the copolymer of the invention is preferably from 5 to 15 wt % because when the content of the constituent unit (C) in the polymer of the invention is within the foregoing range, the water and oil repellency of a surface treatment agent containing the polymer of the invention is improved.

In cases where two or more types of constituent units (C) are present by the use of two or more types of compounds (c), the total content is preferably within the foregoing range.

In formula (d), $Q^3$ is a single bond or a divalent linking group and examples of the divalent linking group include those defined for $Q^1$ in formula (a).

$R^7$ is a hydrogen atom or a methyl group. $R^8$ is an OH group or a group represented by formula (t) shown below:

-$Q^4$-OCO—$CR^9$=$CH_2$  (t)

$Q^4$ is a single bond or a divalent linking group; and
$R^9$ is a hydrogen atom or a methyl group.

$Q^4$ is a single bond or a divalent linking group and examples of the divalent linking group include those defined for $Q^1$ in formula (a). However, the divalent linking group represented by formula (u1) is preferably reversed in the horizontal direction so as to be oriented as "—Z—Y—." "—$(C_2H_4O)_p$— and —$(C_3H_6O)_q$—" (where p and q are each independently from 1 to 10 (on average)) are also preferably reversed in the horizontal direction so as to be oriented as "—$(OC_2H_4)_p$— and —$(OC_3H_6)_q$—" (where p and q are each independently from 1 to 10 (on average)), respectively.

In formula (d), $Q^3$ is preferably a single bond, an alkylene group having 1 to 10 carbon atoms or —$(C_2H_4O)_p$—, and a carbon atom in the group may have a substituent such as ($CH_2Cl$). $R^8$ is preferably an OH group or a group represented by formula (t) in which $Q^4$ is —$(OC_2H_4)_p$— (where p is 1 to 10 (on average)), and most preferably an OH group.

Specific examples of the compound (d) include the following compounds:

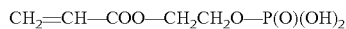

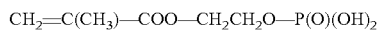

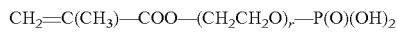

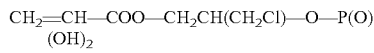

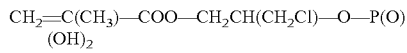

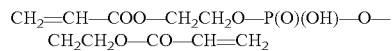

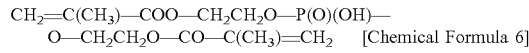 [Chemical Formula 6]

(where r is from 2 to 10 (on average).)

The compound (d) in which $Q^3$ is an alkylene group having 1 to 10 carbon atoms or —$(C_2H_4O)_p$— (where p is from 1 to 10 (on average)), and $R^8$ is an OH group is preferable because the water and oil repellency is improved.

The compounds (d) may be used alone or in combination of two or more thereof.

The content of the constituent unit (D) in the copolymer of the invention is preferably from 0.1 to 5 wt % because when the content of the constituent unit (D) in the polymer of the invention is within the foregoing range, the water and oil repellency of a surface treatment agent containing the polymer of the invention is improved.

In cases where two or more types of constituent units (D) are present by the use of two or more types of compounds (d), the total content is preferably within the foregoing range.

The chain transfer agent (e) contains an OH group or a COOH group. The chain transfer agent is not particularly limited as long as it causes chain transfer in radical polymerization and to be more specific, alcohols and thiols are used. Specific examples include isopropanol, isobutyl alcohol, ethanol, methanol, 2-mercaptoethanol, thioglycerol, thioglycolic acid, and mercaptopropionic acid. Of these, alcohols are preferred because of their low odor and isopropanol is particularly preferred because of its good water and oil repellency.

By using the chain transfer agent (e) during polymerization, a residue (E) of the chain transfer agent (e) having an OH group or a COOH group can be introduced to the end of the main chain of the copolymer of the invention.

The chain transfer agent (e) is preferably used in an amount of 0.05 to 400 parts by weight with respect to the total amount (100 parts by weight) of the compounds (a) to (d). When the chain transfer agent (e) is an alcohol, a small part functions as the chain transfer agent and a large part functions as a solvent. Therefore, in this case, the alcohol content is preferably from 5 to 400 parts by weight. When the chain transfer agent (e) is a thiol, the thiol content is preferably from 0.05 to 20 parts by weight.

The copolymer of the invention may further include a constituent unit (G) derived from a compound (g) in addition to the compounds (a) to (d) described above.

The compound (g) should be copolymerizable with the compounds (a) to (d) and examples thereof include a (meth) acrylic acid ester compound (g1), a styrene compound (g2) and another polymerizable compound (g3). Specific examples of the compound (g) are shown below but the invention is not limited thereto.

An example of the compound (g1) includes a (meth) acrylate represented by formula shown below:

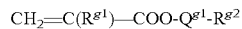

where $R^{g1}$ is a hydrogen atom or a methyl group, $Q^{g1}$ is a single bond or a divalent linking group, and $R^{g2}$ is $Si(OAk)_3$ (where Ak is a linear or branched alkyl group having 1 to 3 carbon atoms), —$CH_3$, —$CH_2CH_2N(CH_3)_2$, —$(CH_2)_mH$ (m is from 2 to 20), —$CH_2CH(CH_3)_2$, —$CH_2$—$C(CH_3)_2$— OCO-Ph, —$CH_2Ph$, —$CH_2CH_2OPh$, —$CH_2N^+(CH_3)_3Cl^-$, —$(CH_2)_2$—NCO,

[Chemical Formula 7]

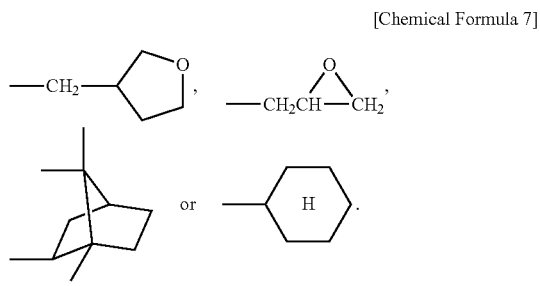

The divalent linking group in $Q^{g1}$ may have the same structure as in $Q^1$ of the compound (a). $Q^{g1}$ is preferably a single bond or a linear or branched alkylene group.

Other examples of the compound (g1) include polyester of (meth)acrylic acid such as diester acrylate and a compound represented by formula shown below:

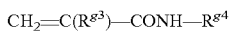

where $R^{g3}$ is a hydrogen atom or a methyl group, and $R^{g4}$ is $-C_mH_{2m+1}$ (m is from 2 to 20) or $-H$.

An example of the compound (g2) includes a styrene compound represented by formula shown below:

[Chemical Formula 8]

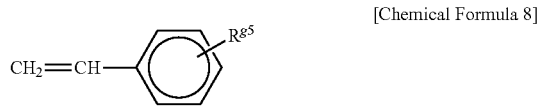

where $R^{g5}$ is $-H$, $CH_3$, $-Cl$, $-CHO$, $-COOH$, $-CH_2Cl$, $-CH_2NH_2$, $-CH_2N(CH_3)_2$, $-CH_2N^+(CH_3)_3Cl^-$, $-CH_2N^+H_3Cl^-$, $-CH_2CN$, $-CH_2COOH$, $-CH_2N(CH_2COOH)_2$, $-CH_2SH$, $-CH_2SO_3Na$ or $-CH_2OCOCH_3$.

Examples of another polymerizable compound (g3) include vinyl compounds other than the compounds (g1) and (g2) such as vinyl chloride ($CH_2$=CHCl) and acrylonitrile ($CH_2$=CHCN).

The content of the constituent unit (G) in the copolymer of the invention is preferably from 0 to 25 wt %. The content of the constituent unit (G) is more preferably from 0 to 10 wt % so as not to deteriorate the water and oil repellency.

The copolymer of the invention is not particularly limited in its polymerization form and may be any of a random copolymer, a block copolymer and a graft copolymer.

In addition, a variety of polymerization methods including bulk polymerization, solution polymerization, suspension polymerization and emulsion polymerization may be adopted.

The copolymer of the invention is obtained by carrying out a polymerization reaction of the respective monomers in a solvent or water using a known method.

Examples of the solvent include ketones (e.g., acetone, methyl ethyl ketone, methyl isobutyl ketone), alcohols (e.g., isopropyl alcohol), esters (e.g., ethyl acetate, butyl acetate), ethers (e.g., diisopropyl ether), aliphatic hydrocarbons or aromatic hydrocarbons, halogenated hydrocarbons (e.g., perchloroethylene, dichloromethane, trichloro-1,1,1-ethane), fluorine solvents (hydrofluorocarbon, hydrofluoroether, m-xylene hexafluoride), N,N-dimethylformamide, N-methylpyrrolidone, dimethyl sulfoxide, glycol ether and derivatives thereof.

The source for initiating the polymerization is not particularly limited and general radical polymerization initiators such as organic peroxides, azo compounds and persulfates may be used. In the case of emulsion polymerization in an aqueous medium, of azo initiators and peroxide initiators, a water-soluble initiator is preferably used.

The molecular weight of the polymer is not particularly limited and the polymer preferably has a weight-average molecular weight ($M_w$) of 1,000 to 1,000,000 and more preferably 2,000 to 100,000.

A surface treatment agent for cosmetics according to the invention contains the copolymer of the invention and a solvent and can be used as a solution containing the copolymer dissolved or dispersed in the solvent. A polymerization solution obtained after polymerization may also be used without further treatment. The solvent is not particularly limited as long as a polymer can be dissolved or dispersed therein and a variety of solvents including water, a hydrocarbon solvent and a fluorine solvent can be used in the same manner as the polymerization solvent. The solvents may be used alone or as a mixture. Of these, water, alcohols (e.g., isopropyl alcohol) and esters (e.g., ethyl acetate and butyl acetate) are preferable.

The concentration of the surface treatment agent of the invention is not particularly limited as long as the concentration is suitable to easily treat cosmetic powder. The copolymer of the invention preferably has a concentration of 0.1 to 40 wt % because cosmetic powder can be easily treated.

A cosmetic powder of the invention is a cosmetic powder including the copolymer of the invention attached to the surfaces of powder particles. The copolymer may be attached to part of the surface of a powder particle or be attached so as to cover the whole surface of a powder particle.

Powder that may be used to manufacture the cosmetic powder of the invention is preferably an inorganic powder, an organic powder or a composite powder of an inorganic power and an organic powder.

Examples of the inorganic powder include silicic acid, silicic anhydride, magnesium silicate, talc, sericite, kaolin, mica, bentonite, titanium-coated mica, bismuth oxychloride, zirconium oxide, magnesium oxide, zinc oxide, titanium dioxide, particulate titanium oxide, aluminum oxide, aluminum hydroxide, calcium sulfate, barium sulfate, magnesium sulfate, calcium carbonate, magnesium carbonate, iron oxide, ultramarine blue, iron blue, chromium oxide, chromium hydroxide, calamine, carbon black and composites thereof.

Examples of the organic powder include polyamides such as nylon, polyester, polyethylene, polypropylene, polystyrene, polyurethane, vinyl resin, urea resin, phenolic resin, fluoro resin, silicone resin, acrylic resin, melamine resin, epoxy resin, polycarbonate resin, divinylbenzene/styrene copolymer and other copolymers, celluloid, acetyl cellulose, cellulose, chitin, chitosan, polysaccharide, protein, C.I. Pigment Yellow, C.I. Pigment Orange, C.I. Pigment Red, C.I. Pigment Violet, C.I. Pigment Blue, C.I. Pigment Green, C.I. Pigment Brown and sugar.

The powders for use in the manufacture of the cosmetic powder of the invention may be used alone or in combination of two or more thereof.

The powder for use in the manufacture of the cosmetic powder of the invention is, for example, in a plate-like, massive, scaly or porous spherical shape. The powder particles may have small holes at the surfaces thereof.

The copolymer of the invention is preferably attached to the powder (powder as the material) in an amount of 0.1 to 50 parts by weight and more preferably 1 to 20 parts by weight with respect to 100 parts by weight of the powder. The amount of attachment is the amount of the copolymer of the invention used to treat the powder. For instance, in a case where 1 g of the powder is treated with 1 g of the surface treatment agent for cosmetics according to the invention containing 3% of the copolymer of the invention, the amount of attachment is 3 parts by weight.

The powder for cosmetics is obtained by treating the surfaces of powder particles with a fluorine-containing copolymer. The treatment method is not particularly limited and a variety of mixing and dispersing methods and drying methods may be used. A specific method involves mixing a powder and a surface treatment agent for dispersion and drying at room temperature or under heating.

The cosmetic powder of the invention may be used as a cosmetic preparation without further treatment or be blended with other ingredients.

Exemplary other ingredients include:
solid or semisolid oils such as vaseline, lanolin, ceresin, microcrystalline wax, carnauba wax, candelilla wax, higher fatty acid, higher alcohol; fluid oils such as squalane, liquid paraffin, ester oil, diglyceride, triglyceride and silicone oil; and fluorine-containing oils such as perfluoropolyether, perfluorodecalin and perfluorooctane; water-soluble or oil-soluble polymers, surfactants; coloring materials such as inorganic or organic pigment, tar dye and natural dye; ethanol, preservative, antioxidant, pigment, thickener, pH adjuster, perfume, UV absorber, humectant, blood circulation promoter, coolant, antiperspirant, germicide, skin activator, water and the like.

These other ingredients can be blended in such qualitative and quantitative ranges that the effects of the invention are not impaired.

Examples of the cosmetic preparation of the invention include makeup cosmetics such as powdery foundation, creamy foundation, oily foundation, dual-use foundation, face powder, blusher, eye shadow and eyebrow liner; and body cosmetics such as body powder and baby powder.

EXAMPLES

Next, the present invention is described more specifically by referring to the Examples, which by no means limit the scope of the present invention. In the following, unless otherwise specified, "parts" and "%" refer to "parts by weight" and "% by weight," respectively.

(Example 1) Preparation of Polymer

An airtight container was charged with 24 g of $C_6F_{13}C_2H_4OCOCH=CH_2$ (hereinafter abbreviated as C6FA), 3 g of acrylic acid, 2.4 g of $CH_2=C(CH_3)COO(C_2H_4O)_nH$ (n has an average value of 4.5; hereinafter abbreviated as EOMA), 0.6 g of $CH_2=C(CH_3)COOC_2H_4OP(O)(OH)_2$ (hereinafter abbreviated as MOEP), 30 g of isopropanol (hereinafter abbreviated as IPA), 30 g of butyl acetate and 0.15 g of an initiator V-601 (dimethyl 2,2'-azobis(2-methyl propionate) manufactured by Wako Pure Chemical Industries, Ltd.) and purged with nitrogen. Then, a polymerization reaction was carried out at 70° C. for 18 hours. The resulting solution was diluted with 30 g of IPA and 30 g of butyl acetate to obtain Polymer (1) as a pale yellow solution having a solid content concentration of 19.1%.

Examples 2 to 4

Polymerization was carried out in the same manner at the monomer weight ratios shown in Table 1, thereby obtaining Polymers (2) to (4).

Comparative Examples 1 to 4

Polymerization was carried out in the same manner at the monomer weight ratios shown in Table 1, thereby obtaining Comparative polymers (1) to (4).

TABLE 1

|  | Polymer (1) | Polymer (2) | Polymer (3) | Polymer (4) | Comparative polymer (1) | Comparative polymer (2) | Comparative polymer (3) | Comparative polymer (4) |
|---|---|---|---|---|---|---|---|---|
| C6FA | 80 | 80 | 80 | 85 | 80 | 80 | 80 | 80 |
| Acrylic acid | 10 | 10 | 10 | 8 |  |  | 10 | 10 |
| EOMA | 8 | 5 | 8 | 5 | 20 | 15 | 10 | 5 |
| MOEP | 2 |  | 2 | 2 |  | 5 |  |  |
| MOE2P |  | 5 |  |  |  |  |  | 5 |
| IPA | 100 | 100 | 50 | 100 | 100 | 100 | 100 |  |
| Butyl acetate | 100 | 100 | 100 | 100 | 100 | 100 | 100 |  |
| MEK |  |  |  |  |  |  |  | 200 |
| V-601 | 0.5 | 0.5 | 0.25 | 0.5 | 0.5 | 0.5 | 0.5 | 0.5 |

MOE2P: $CH_2=C(CH_3)COO(C_2H_4O)_nP(O)(OH)_2$ (n = 4-5)
MEK: Methyl ethyl ketone Example 5

Polymers (1) to (4) obtained in Examples 1 to 4 were each diluted with a mixture solution of IPA and butyl acetate (50/50) to prepare Surface treatment agents (1) to (4) having a solid content concentration of 3%.

Comparative Example 5

Comparative polymers (1) to (4) obtained in Comparative Examples 1 to 4 were diluted in the same manner as in Example 5 to obtain Comparative surface treatment agents (1) to (4).

Example 6

To 1 g each of Surface treatment agents (1) to (4) prepared in Example 5 was separately added 1 g of titanium dioxide or 1 g of sericite as powder and mixing was carried out. The mixture was dried at 120° C. for 1 hour and pulverized to obtain surface-treated powders.

Comparative Example 6

The surfaces of powder particles were treated with Comparative surface treatment agents (1) to (4) in the same manner as in Example 6.
<Evaluation of Water and Oil Repellency>
The surface-treated powders obtained in Example 6 and Comparative Example 6 were each put in a mold and compression-tableted. Water or liquid paraffin was dropped onto the resulting tablets to measure the contact angle. The evaluation results are shown in Table 2.

TABLE 2

|  | Contact angle (degrees) | | | |
|---|---|---|---|---|
|  | Titanium dioxide | | Sericite | |
|  | Water | Liquid paraffin | Water | Liquid paraffin |
| Surface treatment agent (1) | 131 | 116 | 126 | 96 |
| Surface treatment agent (2) | 133 | 118 | 132 | 99 |
| Surface treatment agent (3) | 132 | 115 | 130 | 102 |
| Surface treatment agent (4) | 134 | 118 | 126 | 102 |
| Comparative surface treatment agent (1) | 131 | 102 | 94 | 94 |
| Comparative surface treatment agent (2) | 125 | 100 | 129 | 102 |
| Comparative surface treatment agent (3) | 132 | 118 | 118 | 91 |
| Comparative surface treatment agent (4) | 112 | 62 | 124 | 94 |

It was revealed that, as compared to Comparative surface treatment agents, Surface treatment agents each using the copolymer of the invention impart high water repellency and high oil repellency to any of titanium dioxide powder and sericite powder.

The invention claimed is:

1. A copolymer, comprising:
   75 to 85 wt % of a monomer unit (A) obtained by polymerizing a compound represented by formula (a) shown below;
   5 to 15 wt % of a monomer unit (B) obtained by polymerizing (meth)acrylic acid;
   5 to 15 wt % of a monomer unit (C) obtained by polymerizing a compound represented by formula (c) shown below;
   0.1 to 5 wt % of a monomer unit (D) obtained by polymerizing a compound represented by formula (d) shown below; and
   a residue (E) of a chain transfer agent (e) which is isopropanol, $$CH_2=CR^1-COO-Q^1-Rf \quad (a)$$

where
$Q^1$ is a single bond or a linear or branched alkylene group having 1 to 10 carbon atoms;
$R^1$ is a hydrogen atom; and
Rf is a polyfluoroalkyl group having 4 to 6 carbon atoms, $$CH_2=CR^3-COO-(R^4O)n-R^5 \quad (c)$$

where
$R^3$ is a hydrogen atom or a methyl group;
$R^4$ is $C_2H_4$;
n is a number of from 2 to 10 on average; and
$R^5$ is a hydrogen atom or a methyl group, $$CH_2=CR^7-COO-Q^3-P(O)(OH)-R^8 \quad (d)$$

where
$Q^3$ is $(C_2H_4O)_p$, where p is a number of from 1 to 10 on average;
$R^7$ is a hydrogen atom or a methyl group;
$R^8$ is an OH group.

2. The copolymer according to claim 1, wherein the polyfluoroalkyl group represented by Rf in formula (a) is a perfluoroalkyl group.

3. The copolymer according to claim 1, wherein in formula (c), $R^5$ is a hydrogen atom.

4. The copolymer according to claim 1, wherein the monomer unit (D) is obtained by polymerizing $CH_2=C(CH_3)COOC_2H_4OP(O)(OH)_2$.

5. The copolymer according to claim 1, wherein in formula (a), Rf is polyfluoroalkyl group having 6 carbon atoms.

6. The copolymer according to claim 1, wherein in formula (a), Rf is perfluoroalkyl group having 6 carbon atoms.

7. The copolymer according to claim 1, wherein the monomer unit (D) is obtained by polymerizing $CH_2=C(CH_3)COO(C_2H_4O)_pP(O)(OH)_2$, wherein p is a number of from 1 to 5 on average.

8. The copolymer according to claim 6, wherein the monomer unit (D) is obtained by polymerizing $CH_2=C(CH_3)COO(C_2H_4O)_pP(O)(OH)_2$, wherein p is a number of from 1 to 5 on average.

9. A surface treatment agent, comprising:
   the copolymer according to claim 1, and
   a solvent.

10. A surface-treated cosmetic powder, comprising:
    a cosmetic powder; and
    the copolymer according to claim 1, which is attached to the cosmetic powder.

11. A cosmetic preparation, comprising the surface-treated cosmetic powder according to claim 10.

* * * * *